United States Patent
Jafari et al.

(10) Patent No.: US 8,528,554 B2
(45) Date of Patent: Sep. 10, 2013

(54) INVERSE SAWTOOTH PRESSURE WAVE TRAIN PURGING IN MEDICAL VENTILATORS

(75) Inventors: Medhi M. Jafari, Laguna Hills, CA (US); Jeffrey K. Aviano, Escondido, CA (US); Daniel G. Grabol, Encinitas, CA (US); Edward R. McCoy, Vista, CA (US); Gail F. Upham, Fallbrook, CA (US)

(73) Assignee: Covidien LP, Mansfield, MA (US)

( * ) Notice: Subject to any disclaimer, the term of this patent is extended or adjusted under 35 U.S.C. 154(b) by 995 days.

(21) Appl. No.: 12/553,568

(22) Filed: Sep. 3, 2009

(65) Prior Publication Data

US 2010/0051029 A1    Mar. 4, 2010

Related U.S. Application Data

(60) Provisional application No. 61/169,976, filed on Apr. 16, 2009, provisional application No. 61/094,377, filed on Sep. 4, 2008.

(51) Int. Cl.
*A61M 16/00* (2006.01)

(52) U.S. Cl.
CPC ..................... *A61M 16/00* (2013.01)
USPC ............ 128/204.23; 128/204.21; 128/204.18; 128/200.24

(58) Field of Classification Search
USPC ............. 128/204.23, 200.24, 204.18, 205.23, 128/897, 898; 73/232–281, 861–861.94, 73/1.01–1.89, 23.2–31.07, 861.52
See application file for complete search history.

(56) References Cited

U.S. PATENT DOCUMENTS

| | | | |
|---|---|---|---|
| 4,445,012 A * | 4/1984 | Blackburn et al. | 200/61.04 |
| 4,752,089 A | 6/1988 | Carter | |
| 4,838,259 A | 6/1989 | Gluck et al. | |
| 4,921,642 A | 5/1990 | LaTorraca | |
| 4,954,799 A | 9/1990 | Kumar | |
| 5,038,621 A | 8/1991 | Stupecky | |
| 5,057,822 A | 10/1991 | Hoffman | |
| 5,072,737 A | 12/1991 | Goulding | |
| 5,146,092 A | 9/1992 | Apperson et al. | |
| 5,150,291 A | 9/1992 | Cummings et al. | |
| 5,153,436 A | 10/1992 | Apperson et al. | |
| 5,161,525 A | 11/1992 | Kimm et al. | |
| 5,237,987 A | 8/1993 | Anderson et al. | |

(Continued)

FOREIGN PATENT DOCUMENTS

| | | |
|---|---|---|
| EP | 0728493 | 8/1996 |
| EP | 850652 A2 | 7/1998 |

(Continued)

OTHER PUBLICATIONS

International Search Report, PCT/US2009/055887, dated Feb. 16, 2010.

(Continued)

*Primary Examiner* — Annette Dixon (57) ABSTRACT

This disclosure describes systems and methods for purging narrow diameter sensor tubing, occasionally referred to as "sensor lines," in a ventilation system. The disclosure describes a novel approach in which a series of short, periodic releases of pressurized gas through the sensor tubes are used to clear any blockages due to condensation or patient secretions.

51 Claims, 5 Drawing Sheets

(56) References Cited

U.S. PATENT DOCUMENTS

| | | |
|---|---|---|
| 5,271,389 A | 12/1993 | Isaza et al. |
| 5,279,549 A | 1/1994 | Ranford |
| 5,299,568 A | 4/1994 | Forare et al. |
| 5,301,921 A | 4/1994 | Kumar |
| 5,303,698 A | 4/1994 | Tobia et al. |
| 5,316,009 A | 5/1994 | Yamada |
| 5,319,540 A | 6/1994 | Isaza et al. |
| 5,325,861 A | 7/1994 | Goulding |
| 5,333,606 A | 8/1994 | Schneider et al. |
| 5,339,807 A | 8/1994 | Carter |
| 5,343,857 A | 9/1994 | Schneider et al. |
| 5,351,522 A | 10/1994 | Lura |
| 5,357,946 A | 10/1994 | Kee et al. |
| 5,368,019 A | 11/1994 | Latorraca |
| 5,369,277 A | 11/1994 | Knodle et al. |
| 5,383,449 A | 1/1995 | Forare et al. |
| 5,385,142 A | 1/1995 | Brady et al. |
| 5,390,666 A | 2/1995 | Kimm et al. |
| 5,401,135 A | 3/1995 | Stoen et al. |
| 5,402,796 A | 4/1995 | Packer et al. |
| 5,407,174 A | 4/1995 | Kumar |
| 5,413,110 A | 5/1995 | Cummings et al. |
| 5,438,980 A | 8/1995 | Phillips |
| 5,443,075 A | 8/1995 | Holscher |
| 5,513,631 A | 5/1996 | McWilliams |
| 5,517,983 A | 5/1996 | Deighan et al. |
| 5,520,071 A | 5/1996 | Jones |
| 5,524,615 A | 6/1996 | Power |
| 5,531,221 A | 7/1996 | Power |
| 5,542,415 A | 8/1996 | Brady |
| 5,544,674 A | 8/1996 | Kelly |
| 5,549,106 A | 8/1996 | Gruenke et al. |
| 5,596,984 A | 1/1997 | O'Mahoney et al. |
| 5,616,923 A | 4/1997 | Rich et al. |
| 5,630,411 A | 5/1997 | Holscher |
| 5,632,270 A | 5/1997 | O'Mahoney et al. |
| 5,645,048 A | 7/1997 | Brodsky et al. |
| 5,660,171 A | 8/1997 | Kimm et al. |
| 5,664,560 A | 9/1997 | Merrick et al. |
| 5,664,562 A | 9/1997 | Bourdon |
| 5,671,767 A | 9/1997 | Kelly |
| 5,672,041 A | 9/1997 | Ringdahl et al. |
| 5,673,689 A | 10/1997 | Power |
| 5,693,944 A | 12/1997 | Rich |
| 5,715,812 A | 2/1998 | Deighan et al. |
| 5,762,480 A | 6/1998 | Adahan |
| 5,771,884 A | 6/1998 | Yarnall et al. |
| 5,789,660 A | 8/1998 | Kofoed et al. |
| 5,791,339 A | 8/1998 | Winter |
| 5,794,986 A | 8/1998 | Gansel et al. |
| 5,813,399 A | 9/1998 | Isaza et al. |
| 5,826,575 A | 10/1998 | Lall |
| 5,829,441 A | 11/1998 | Kidd et al. |
| 5,864,938 A | 2/1999 | Gansel et al. |
| 5,865,168 A | 2/1999 | Isaza |
| 5,881,717 A | 3/1999 | Isaza |
| 5,881,723 A | 3/1999 | Wallace et al. |
| 5,884,623 A | 3/1999 | Winter |
| 5,906,204 A | 5/1999 | Beran et al. |
| 5,909,731 A | 6/1999 | O'Mahony et al. |
| 5,915,379 A | 6/1999 | Wallace et al. |
| 5,915,380 A | 6/1999 | Wallace et al. |
| 5,915,382 A | 6/1999 | Power |
| 5,918,597 A | 7/1999 | Jones et al. |
| 5,921,238 A | 7/1999 | Bourdon |
| 5,934,274 A | 8/1999 | Merrick et al. |
| 6,024,089 A | 2/2000 | Wallace et al. |
| 6,041,780 A | 3/2000 | Richard et al. |
| 6,047,860 A | 4/2000 | Sanders |
| 6,076,523 A | 6/2000 | Jones et al. |
| 6,095,140 A | 8/2000 | Poon et al. |
| 6,099,481 A | 8/2000 | Daniels et al. |
| 6,106,480 A | 8/2000 | Gama De Abreu et al. |
| 6,116,240 A | 9/2000 | Merrick et al. |
| 6,116,464 A | 9/2000 | Sanders |
| 6,123,073 A | 9/2000 | Schlawin et al. |
| 6,135,106 A | 10/2000 | Dirks et al. |
| 6,142,150 A | 11/2000 | O'Mahony et al. |
| 6,155,986 A | 12/2000 | Brydon et al. |
| 6,161,539 A | 12/2000 | Winter |
| 6,179,784 B1 | 1/2001 | Daniels et al. |
| 6,203,502 B1 * | 3/2001 | Hilgendorf et al. ............ 600/538 |
| 6,220,245 B1 | 4/2001 | Takabayashi et al. |
| 6,227,196 B1 | 5/2001 | Jaffe et al. |
| 6,269,812 B1 | 8/2001 | Wallace et al. |
| 6,273,444 B1 | 8/2001 | Power |
| 6,283,119 B1 | 9/2001 | Bourdon |
| 6,305,373 B1 | 10/2001 | Wallace et al. |
| 6,306,098 B1 | 10/2001 | Orr et al. |
| 6,312,389 B1 | 11/2001 | Kofoed et al. |
| 6,321,748 B1 | 11/2001 | O'Mahoney |
| 6,325,785 B1 | 12/2001 | Babkes et al. |
| 6,325,978 B1 | 12/2001 | Labuda et al. |
| 6,357,438 B1 | 3/2002 | Hansen |
| 6,358,215 B1 | 3/2002 | Ricciardelli |
| 6,360,745 B1 | 3/2002 | Wallace et al. |
| 6,369,838 B1 | 4/2002 | Wallace et al. |
| 6,390,091 B1 | 5/2002 | Banner et al. |
| 6,394,962 B1 | 5/2002 | Gama De Abreu et al. |
| 6,402,697 B1 | 6/2002 | Calkins et al. |
| 6,408,848 B1 | 6/2002 | Feldman et al. |
| 6,412,483 B1 | 7/2002 | Jones et al. |
| 6,439,229 B1 | 8/2002 | Du et al. |
| 6,467,478 B1 | 10/2002 | Merrick et al. |
| 6,471,658 B1 | 10/2002 | Daniels et al. |
| 6,540,689 B1 | 4/2003 | Orr et al. |
| 6,546,930 B1 | 4/2003 | Emerson et al. |
| 6,553,991 B1 | 4/2003 | Isaza |
| 6,557,553 B1 | 5/2003 | Borrello |
| 6,571,795 B2 | 6/2003 | Bourdon |
| 6,575,164 B1 | 6/2003 | Jaffe et al. |
| 6,616,896 B2 | 9/2003 | Apperson et al. |
| 6,622,726 B1 | 9/2003 | Du |
| 6,629,934 B2 | 10/2003 | Mault et al. |
| 6,644,310 B1 | 11/2003 | Delache et al. |
| 6,648,831 B2 | 11/2003 | Orr et al. |
| 6,648,832 B2 | 11/2003 | Orr et al. |
| 6,659,962 B2 | 12/2003 | Ricciardelli |
| 6,668,824 B1 | 12/2003 | Isaza et al. |
| 6,675,801 B2 | 1/2004 | Wallace et al. |
| 6,718,974 B1 | 4/2004 | Moberg |
| 6,725,447 B1 | 4/2004 | Gilman et al. |
| 6,739,337 B2 | 5/2004 | Isaza |
| 6,761,167 B1 | 7/2004 | Nadjafizadeh et al. |
| 6,761,168 B1 | 7/2004 | Nadjafizadeh et al. |
| 6,763,829 B2 | 7/2004 | Jaffe et al. |
| 6,802,225 B2 | 10/2004 | Shahar et al. |
| 6,814,074 B1 | 11/2004 | Nadjafizadeh et al. |
| 6,815,211 B1 | 11/2004 | Blazewicz et al. |
| 6,840,906 B2 | 1/2005 | Gama De Abreu et al. |
| 6,866,040 B1 | 3/2005 | Bourdon |
| 6,908,438 B2 | 6/2005 | Orr et al. |
| 6,945,123 B1 | 9/2005 | Kuehl |
| 6,954,702 B2 | 10/2005 | Pierry et al. |
| 6,955,651 B2 | 10/2005 | Kück et al. |
| 6,960,854 B2 | 11/2005 | Nadjafizadeh et al. |
| 6,990,980 B2 | 1/2006 | Richey, II |
| 7,004,168 B2 | 2/2006 | Mace et al. |
| 7,018,340 B2 | 3/2006 | Jaffe et al. |
| 7,032,463 B2 | 4/2006 | Misholi et al. |
| 7,036,504 B2 | 5/2006 | Wallace et al. |
| 7,066,176 B2 | 6/2006 | Jaffe et al. |
| 7,074,196 B2 | 7/2006 | Kück et al. |
| 7,077,131 B2 | 7/2006 | Hansen |
| RE39,225 E | 8/2006 | Isaza et al. |
| 7,117,438 B2 | 10/2006 | Wallace et al. |
| 7,135,001 B2 | 11/2006 | Orr et al. |
| 7,183,552 B2 | 2/2007 | Russell |
| 7,270,126 B2 | 9/2007 | Wallace et al. |
| 7,291,851 B2 | 11/2007 | DelFavero et al. |
| 7,335,164 B2 | 2/2008 | Mace et al. |
| 7,341,563 B2 | 3/2008 | Rich et al. |
| 7,347,205 B2 | 3/2008 | Levi |
| 7,369,757 B2 | 5/2008 | Farbarik |

| | | |
|---|---|---|
| 7,370,650 B2 | 5/2008 | Nadjafizadeh et al. |
| 7,427,269 B2 | 9/2008 | George et al. |
| 7,428,902 B2 | 9/2008 | Du et al. |
| 7,432,508 B2 | 10/2008 | Daniels et al. |
| 7,460,959 B2 | 12/2008 | Jafari |
| 7,487,773 B2 | 2/2009 | Li |
| 7,509,957 B2 | 3/2009 | Duquette et al. |
| 7,607,360 B2 | 10/2009 | Todokoro et al. |
| 7,654,802 B2 | 2/2010 | Crawford, Jr. et al. |
| 7,694,677 B2 | 4/2010 | Tang |
| 7,717,113 B2 | 5/2010 | Andrieux |
| 7,721,736 B2 | 5/2010 | Urias et al. |
| D618,356 S | 6/2010 | Ross |
| 7,784,461 B2 | 8/2010 | Figueiredo et al. |
| 7,799,231 B2 | 9/2010 | Irvine |
| 7,823,588 B2 | 11/2010 | Hansen |
| 7,855,716 B2 | 12/2010 | McCreary et al. |
| D632,796 S | 2/2011 | Ross et al. |
| D632,797 S | 2/2011 | Ross et al. |
| 7,891,354 B2 | 2/2011 | Farbarik |
| 7,893,560 B2 | 2/2011 | Carter |
| D638,852 S | 5/2011 | Skidmore et al. |
| 7,984,714 B2 | 7/2011 | Hausmann et al. |
| D643,535 S | 8/2011 | Ross et al. |
| 7,992,557 B2 | 8/2011 | Nadjafizadeh et al. |
| 8,001,967 B2 | 8/2011 | Wallace et al. |
| 8,021,310 B2 | 9/2011 | Sanborn et al. |
| D649,157 S | 11/2011 | Skidmore et al. |
| 8,113,062 B2 | 2/2012 | Graboi et al. |
| 8,181,648 B2 | 5/2012 | Perine et al. |
| 8,210,173 B2 | 7/2012 | Vandine |
| 8,210,174 B2 | 7/2012 | Farbarik |
| 8,240,684 B2 | 8/2012 | Ross et al. |
| 8,267,085 B2 | 9/2012 | Jafari et al. |
| 8,272,379 B2 | 9/2012 | Jafari et al. |
| 8,272,380 B2 | 9/2012 | Jafari et al. |
| 8,302,600 B2 | 11/2012 | Andrieux et al. |
| 8,302,602 B2 | 11/2012 | Andrieux et al. |
| 2001/0029339 A1 | 10/2001 | Orr et al. |
| 2001/0031928 A1 | 10/2001 | Orr et al. |
| 2002/0053345 A1 | 5/2002 | Jafari et al. |
| 2002/0103444 A1 | 8/2002 | Ricciardelli |
| 2002/0116994 A1 | 8/2002 | Heinonen |
| 2002/0128566 A1 | 9/2002 | Gama De Abreu et al. |
| 2003/0047188 A1 | 3/2003 | Mace et al. |
| 2003/0168060 A1* | 9/2003 | Richardson et al. ...... 128/201.24 |
| 2003/0191405 A1 | 10/2003 | Rich et al. |
| 2004/0003814 A1 | 1/2004 | Banner et al. |
| 2004/0087867 A1 | 5/2004 | Gama De Abreu et al. |
| 2004/0133123 A1 | 7/2004 | Leonhardt et al. |
| 2004/0186391 A1 | 9/2004 | Pierry et al. |
| 2004/0256560 A1 | 12/2004 | Russell |
| 2005/0039748 A1 | 2/2005 | Andrieux |
| 2005/0139212 A1 | 6/2005 | Bourdon |
| 2005/0154320 A1 | 7/2005 | Froelich et al. |
| 2005/0241640 A1 | 11/2005 | Baecke et al. |
| 2005/0279358 A1 | 12/2005 | Richey, II |
| 2005/0285055 A1 | 12/2005 | Defavero et al. |
| 2006/0009707 A1 | 1/2006 | Daniels et al. |
| 2006/0052950 A1 | 3/2006 | Pierry et al. |
| 2006/0086357 A1 | 4/2006 | Soliman et al. |
| 2006/0129054 A1 | 6/2006 | Orr et al. |
| 2006/0145078 A1 | 7/2006 | Russell |
| 2006/0241508 A1 | 10/2006 | Jaffe et al. |
| 2006/0249153 A1 | 11/2006 | DeVries et al. |
| 2006/0253038 A1 | 11/2006 | Kück et al. |
| 2007/0017515 A1 | 1/2007 | Wallace et al. |
| 2007/0044798 A1 | 3/2007 | Levi |
| 2007/0068518 A1 | 3/2007 | Urias et al. |
| 2007/0077200 A1 | 4/2007 | Baker |
| 2007/0107728 A1 | 5/2007 | Ricciardelli et al. |
| 2007/0142716 A1 | 6/2007 | Biondi |
| 2007/0149891 A1 | 6/2007 | George et al. |
| 2007/0157930 A1 | 7/2007 | Soliman et al. |
| 2007/0193579 A1 | 8/2007 | Duquette et al. |
| 2007/0199566 A1 | 8/2007 | Be'eri |
| 2007/0225612 A1 | 9/2007 | Mace et al. |
| 2007/0227537 A1 | 10/2007 | Bemister et al. |
| 2007/0272241 A1 | 11/2007 | Sanborn et al. |
| 2007/0272242 A1 | 11/2007 | Sanborn et al. |
| 2007/0273887 A1 | 11/2007 | Russell |
| 2007/0282214 A1 | 12/2007 | George et al. |
| 2007/0284361 A1 | 12/2007 | Nadjafizadeh et al. |
| 2008/0006266 A1* | 1/2008 | Bolam ..................... 128/200.24 |
| 2008/0021339 A1 | 1/2008 | Gabriel et al. |
| 2008/0053441 A1 | 3/2008 | Gottlib et al. |
| 2008/0058667 A1 | 3/2008 | Pierry et al. |
| 2008/0072896 A1 | 3/2008 | Setzer et al. |
| 2008/0072902 A1 | 3/2008 | Setzer et al. |
| 2008/0078390 A1 | 4/2008 | Milne et al. |
| 2008/0083644 A1 | 4/2008 | Janbakhsh et al. |
| 2008/0091117 A1 | 4/2008 | Choncholas et al. |
| 2008/0092894 A1 | 4/2008 | Nicolazzi et al. |
| 2008/0097234 A1 | 4/2008 | Nicolazzi et al. |
| 2008/0119753 A1 | 5/2008 | Ricciardelli et al. |
| 2008/0119754 A1 | 5/2008 | Hietala |
| 2009/0165795 A1 | 7/2009 | Nadjafizadeh et al. |
| 2009/0171176 A1 | 7/2009 | Andersohn |
| 2009/0205661 A1 | 8/2009 | Stephenson et al. |
| 2009/0205663 A1 | 8/2009 | Vandine et al. |
| 2009/0241952 A1 | 10/2009 | Nicolazzi et al. |
| 2009/0241953 A1 | 10/2009 | Vandine et al. |
| 2009/0241956 A1 | 10/2009 | Baker, Jr. et al. |
| 2009/0241957 A1 | 10/2009 | Baker, Jr. |
| 2009/0241958 A1 | 10/2009 | Baker, Jr. |
| 2009/0241962 A1 | 10/2009 | Jafari et al. |
| 2009/0247891 A1 | 10/2009 | Wood |
| 2009/0293876 A1 | 12/2009 | Soliman et al. |
| 2009/0301486 A1 | 12/2009 | Masic |
| 2009/0301487 A1 | 12/2009 | Masic |
| 2009/0301490 A1 | 12/2009 | Masic |
| 2009/0301491 A1 | 12/2009 | Masic et al. |
| 2010/0011307 A1 | 1/2010 | Desfossez et al. |
| 2010/0024820 A1 | 2/2010 | Bourdon |
| 2010/0051026 A1 | 3/2010 | Graboi |
| 2010/0069761 A1 | 3/2010 | Karst et al. |
| 2010/0071689 A1 | 3/2010 | Thiessen |
| 2010/0071692 A1 | 3/2010 | Porges |
| 2010/0071695 A1 | 3/2010 | Thiessen |
| 2010/0071696 A1 | 3/2010 | Jafari |
| 2010/0071697 A1 | 3/2010 | Jafari et al. |
| 2010/0077866 A1 | 4/2010 | Graboi et al. |
| 2010/0078017 A1 | 4/2010 | Andrieux et al. |
| 2010/0078026 A1 | 4/2010 | Andrieux et al. |
| 2010/0081119 A1 | 4/2010 | Jafari et al. |
| 2010/0081955 A1 | 4/2010 | Wood, Jr. et al. |
| 2010/0139660 A1 | 6/2010 | Adahan |
| 2010/0147303 A1 | 6/2010 | Jafari et al. |
| 2010/0218765 A1 | 9/2010 | Jafari et al. |
| 2010/0218766 A1 | 9/2010 | Milne |
| 2010/0218767 A1 | 9/2010 | Jafari et al. |
| 2010/0236555 A1 | 9/2010 | Jafari et al. |
| 2010/0242961 A1 | 9/2010 | Mougel et al. |
| 2010/0288283 A1 | 11/2010 | Campbell et al. |
| 2010/0300446 A1 | 12/2010 | Nicolazzi et al. |
| 2011/0011400 A1 | 1/2011 | Gentner et al. |
| 2011/0023879 A1 | 2/2011 | Vandine et al. |
| 2011/0041849 A1 | 2/2011 | Chen et al. |
| 2011/0126832 A1 | 6/2011 | Winter et al. |
| 2011/0126834 A1 | 6/2011 | Winter et al. |
| 2011/0126835 A1 | 6/2011 | Winter et al. |
| 2011/0126836 A1 | 6/2011 | Winter et al. |
| 2011/0126837 A1 | 6/2011 | Winter et al. |
| 2011/0138308 A1 | 6/2011 | Palmer et al. |
| 2011/0138309 A1 | 6/2011 | Skidmore et al. |
| 2011/0138311 A1 | 6/2011 | Palmer |
| 2011/0138323 A1 | 6/2011 | Skidmore et al. |
| 2011/0146681 A1 | 6/2011 | Jafari et al. |
| 2011/0146683 A1 | 6/2011 | Jafari et al. |
| 2011/0175728 A1 | 7/2011 | Baker, Jr. |
| 2011/0209702 A1 | 9/2011 | Vuong et al. |
| 2011/0209704 A1 | 9/2011 | Jafari et al. |
| 2011/0209707 A1 | 9/2011 | Terhark |
| 2011/0213215 A1 | 9/2011 | Doyle et al. |
| 2011/0259330 A1 | 10/2011 | Jafari et al. |

FOREIGN PATENT DOCUMENTS

| | | |
|---|---|---|
| EP | 1228779 | 8/2002 |
| EP | 2025358 | 2/2009 |
| EP | 2106818 | 10/2009 |
| JP | 2002136595 | 5/2002 |
| WO | WO9641571 | 12/1996 |
| WO | WO9744636 | 11/1997 |
| WO | WO 98/41268 | 9/1998 |
| WO | WO2007/109177 | 9/2007 |
| WO | WO 2007/109177 | 9/2007 |
| WO | WO 2008/042790 | 4/2008 |
| WO | WO 2009/063446 | 5/2009 |
| WO | WO 2009/123973 | 10/2009 |

OTHER PUBLICATIONS

International Search Report, PCT/US2009/059102, dated Nov. 30, 2009.

International Search Report, PCT/US200905589, dated Nov. 26, 2009.

U.S. Appl. No. 12/570,956, Notice of Allowance mailed Sep. 21, 2011, 8 pgs.

7200 Series Ventilator, Options, and Accessories: Operator's Manual. Nellcor Puritan Bennett, Part No. 22300 A, Sep. 1990, pp. 1-196.

7200 Ventilatory System: Addendum/Errata. Nellcor Puritan Bennett, Part No. 4-023576-00, Rev. A, Apr. 1988, pp. 1-32.

800 Operator's and Technical Reference Manual. Series Ventilator System, Nellcor Puritan Bennett, Part No. 4-070088-00, Rev. L, Aug. 2010, pp. 1-476.

840 Operator's and Technical Reference Manuel. Ventilator System, Nellcor Puritan Bennett, Part No. 4-075609-00, Rev. G, Oct. 2006, pp. 1-424.

Jaffe, Ph.D., "Flow Proximal Measurement with Series 3 Flow Sensors—Technical Issues", Respironics Novametrix, Inc., pp. 1-4, 1012246 SB, Sep. 27, 2002.

PCT International Search Report, Date of Mailing Feb. 1, 2011, Applicant's file reference H-RM-01865WO, International Application No. PCT/US2010/058487, International Filing Date Dec. 1, 2010, 11 pgs.

U.S. Appl. No. 12/570,956, filed Sep. 30, 2009, Office Action mailed Mar. 3, 2011, 8 pgs.

U.S. Appl. No. 12/570,956, filed Sep. 30, 2009, Notice of Allowance mailed Jul. 19, 2011, 7 pgs.

PCT International Search Report mailed Aug. 2, 2011; International Application No. PCT/US2011/025365, 12 pgs.

U.S. Appl. No. 12/553,576, Office Action mailed Aug. 13, 2012, 17 pgs.

U.S. Appl. No. 12/643,083, Office Action mailed Mar. 13, 2013, 11 pgs.

U.S. Appl. No. 12/713,483, Office Action mailed Mar. 13, 2013, 12 pgs.

U.S. Appl. No. 12/553,576, Office Action mailed May 17, 2013, 10 pgs.

* cited by examiner

INVERSE SAWTOOTH PRESSURE WAVE TRAIN PURGING IN MEDICAL VENTILATORS

RELATED APPLICATIONS

This application claims the benefit of U.S. Provisional Application No. 61/094,377 filed Sep. 4, 2008 and U.S. Provisional Application No. 61/169,976 filed Apr. 16, 2009, which applications are hereby incorporated herein by reference.

INTRODUCTION

Medical ventilators may determine when a patient takes a breath in order to synchronize the operation of the ventilator with the natural breathing of the patient. In some instances, detection of the onset of inhalation and/or exhalation may be used to trigger one or more actions on the part of the ventilator.

In order to accurately detect the onset of inhalation and/or exhalation, and/or obtain a more accurate measurement of inspiratory and expiratory flow/volume, a flow or pressure sensor may be located close to the patient. For example, to achieve accurate and timely non-invasive signal measurements, differential-pressure flow transducers may be placed at the patient wye proximal to the patient. However, the ventilator circuit and particularly the patient wye is a challenging environment to make continuously accurate measurements. The harsh environment for the sensor is caused, at least in part, by the condensations resulting from the passage of humidified gas through the system as well as secretions emanating from the patient. Over time, the condensate material can enter the sensor tubes and/or block its ports and subsequently jeopardize the functioning of the sensor.

SUMMARY

This disclosure describes systems and methods for purging narrow diameter sensor tubing, occasionally referred to as "sensor lines," in a ventilation system. The disclosure describes a novel approach in which a series of short, periodic releases of pressurized gas through the sensor tubes are used to clear any blockages due to condensation and/or patient secretions.

In part, this disclosure describes a method of purging a sensor tube connecting a patient circuit of a medical ventilator to a sensor. The method includes repeatedly discharging gas through a first sensor tube into the patient circuit. Each purge episode is a cycle of multiple purges in that it consists of a definite number, for example 4, of charge/discharge periods, and because of the short durations that could be allocated to purging, each gas discharge may have a fixed duration of less than, for example, 100 milliseconds and each gas discharge may be separated from the prior gas discharge by not more than, for example, 300 milliseconds.

The disclosure also describes another method of purging two or more sensor tubes in a medical ventilator providing ventilation to a patient. The method includes performing the following steps:
 a) charging a vessel with gas for a fixed period of time or to a first predetermined pressure; and
 b) detecting initiation of a first exhalation phase in the breathing cycle of the patient (or, alternatively, any predetermined point in the breathing cycle of the patient); and then initiating a purge cycle comprising the following steps performed in order:
 c) releasing gas from the vessel through a first one of the sensor tubes into a patient circuit of the ventilator for a first predetermined period of time;
 d) recharging the vessel with gas for a predetermined duration;
 e) releasing gas from the vessel through a second one of the sensor tubes into a patient circuit of the ventilator for a second predetermined period of time;
 f) repeating step d) by again recharging the vessel with gas;
 g) repeating steps c), d) and e); and
 h) repeating steps f) and g) at least once until each tube has been purged, that is received a pulse of gas, a predetermined number of times.

Yet another aspect of this disclosure describes a pressure support system that includes: a pressure generating system adapted to generate a flow of breathing gas; a ventilation system including a patient circuit; at least one circuit sensor in fluid communication with the patient circuit via one or more sensor tubes; and a sensor tube purge module adapted to initiate a purge cycle that purges the sensor tubes. Each purge cycle includes repeatedly discharging gas through the sensor tubes into the patient circuit. Again, each gas discharge may be of a fixed duration of less than, for example, 100 milliseconds and each gas discharge may be separated from the prior gas discharge by not more than, for example, 300 milliseconds.

The disclosure further describes a controller for a medical ventilator that includes a microprocessor; and a sensor tube purge module adapted to initiate a purge cycle that purges sensor tubes connected to sensors in the medical ventilator. Each purge cycle includes repeatedly discharging gas through the sensor tubes into a patient circuit.

In yet another aspect, the disclosure describes a computer-readable medium storing computer-executable instruction for performing a method of purging a sensor tube connecting a patient circuit of a medical ventilator to a sensor in which the method includes repeatedly discharging gas through a first sensor tube into the patient circuit.

In yet another aspect, the disclosure describes a medical ventilator system that includes a processor; a gas regulator in communication with the processor, the gas regulator adapted to regulate a flow of gas from a gas supply to a patient via a patient circuit; a flow sensor package disposed in the patient circuit, the flow sensor package in communication with a gas accumulator; and a pressure sensor coupled to the gas accumulator and in communication with the processor, the pressure sensor adapted to provide pressure readings in the gas accumulator to the processor.

These and various other features as well as advantages which characterize the systems and methods described herein will be apparent from a reading of the following detailed description and a review of the associated drawings. Additional features are set forth in the description which follows, and in part will be apparent from the description, or may be learned by practice of the technology. The benefits and features of the technology will be realized and attained by the structure particularly pointed out in the written description and claims hereof as well as the appended drawings.

It is to be understood that both the foregoing general description and the following detailed description are exemplary and explanatory and are intended to provide further explanation of the invention as claimed.

BRIEF DESCRIPTION OF THE DRAWINGS

The following drawing figures, which form a part of this application, are illustrative of described technology and are

DETAILED DESCRIPTION

Although the techniques introduced above and discussed in detail below may be implemented for a variety of medical devices, the present disclosure will discuss the implementation of these techniques in the context of a medical ventilator for use in providing ventilation support to a human patient. The reader will understand that the technology described in the context of a medical ventilator for human patients could be adapted for use with other systems such as ventilators for non-human patients and general gas transport systems in which sensor tubes in challenging environments may require periodic or occasional purging.

Medical ventilators are used to provide a breathing gas to a patient who may otherwise be unable to breathe sufficiently. In modern medical facilities, pressurized air and oxygen sources are often available from wall outlets. Accordingly, ventilators may provide pressure regulating valves (or regulators) connected to centralized sources of pressurized air and pressurized oxygen. The regulating valves function to regulate flow so that respiratory gas having a desired concentration of oxygen is supplied to the patient at desired pressures and rates. Ventilators capable of operating independently of external sources of pressurized air are also available.

While operating a ventilator, it is desirable to monitor the rate at which breathing gas is supplied to the patient. Accordingly, systems typically have interposed flow and/or pressure sensors. The sensors may be connected to or in communication with the inspiratory limb and the expiratory limb of the ventilator and/or patient circuit. In some cases, it is desirable to provide a flow sensor and/or pressure sensor near the wye of the patient circuit, which connects the inspiratory limb and the expiratory limb near the patient interface (e.g., an endotracheal tube, mask, or the like). Such a sensor package may be referred to as a proximal sensor system, device or module.

When a proximal sensor monitoring device is integrated with a ventilator, it is desirable to add functionality to coordinate the operation of the system as an integrated whole. In addition, functionality can be added to provide more information to ensure satisfactory operation of proximal sensor monitoring at all times. The addition of such improvements can result in an integrated system well-tuned to the features of the ventilator, with higher reliability, improved performance, and consequently, improved patient outcomes.

During operation, the patient circuit can acquire exhaled condensate from the patient and/or condensate from the action of a humidifier in the patient circuit. For circuits containing a proximal flow sensor package which measures flow using the principle of differential pressure, the presence of such liquid or viscous material in either or both of the lines used to sense differential pressure can reduce sensor performance. One approach to address this issue involves sending a puff, pocket, or discharge of air down each of the differential pressure sensing tubes. Such a discharge, which may also be referred to as a single or individual purge of the tube, may help remove or prevent unwanted condensate or the like from the tubes and/or from the proximal flow sensor package. Depending on the embodiment, purging is performed using a sensor tube purge system or module which may be integral with the proximal sensor module or a separate and independent system.

An underlying rationale for the methods and systems described herein can be described as follows. In macroscopic scale aerodynamic systems, the surface tension, surface elasticity, and surface viscosity may be insignificant. However, in systems with smaller dimensions, for example smaller than one (1) centimeter (cm), the surface forces are no longer negligible and can influence the transport process. As dimensions decrease to about one-tenth (0.1) cm, accounting for surface tension and contact angles becomes significant in studying the movement of a wetting liquid in a small diameter tube. The movement of a bolus of liquid in a small diameter tube in the presence of pressure and temperature gradients caused by heated and humidified gas passage is covered by complex phenomena. Two forces acting on a moving body in a fluid environment are drag and lift. The drag force is opposed by a propulsive force in the direction exerted by the purge flow. The net advance of a bolus caused by the purge flow is a function of the maximum purge force generated, the resisting forces, and the distance to be traveled. When small accumulators are used for purging, the charged accumulator will release quickly and there is no significant advantage in prolonging the purge period beyond the initial release. Therefore, purge effectiveness would be significantly increased when the pressure source is left on during a purge cycle and the accumulator is periodically discharged through the sensor tube. This allows the release valve opening and closing to be timed such that the time the valve is open matches the transition time of the peak accumulator pressure to a lower level and the time the valve is closed matches the minimum time required to recharge the accumulator to an adequate or set pressure.

Figure 5:
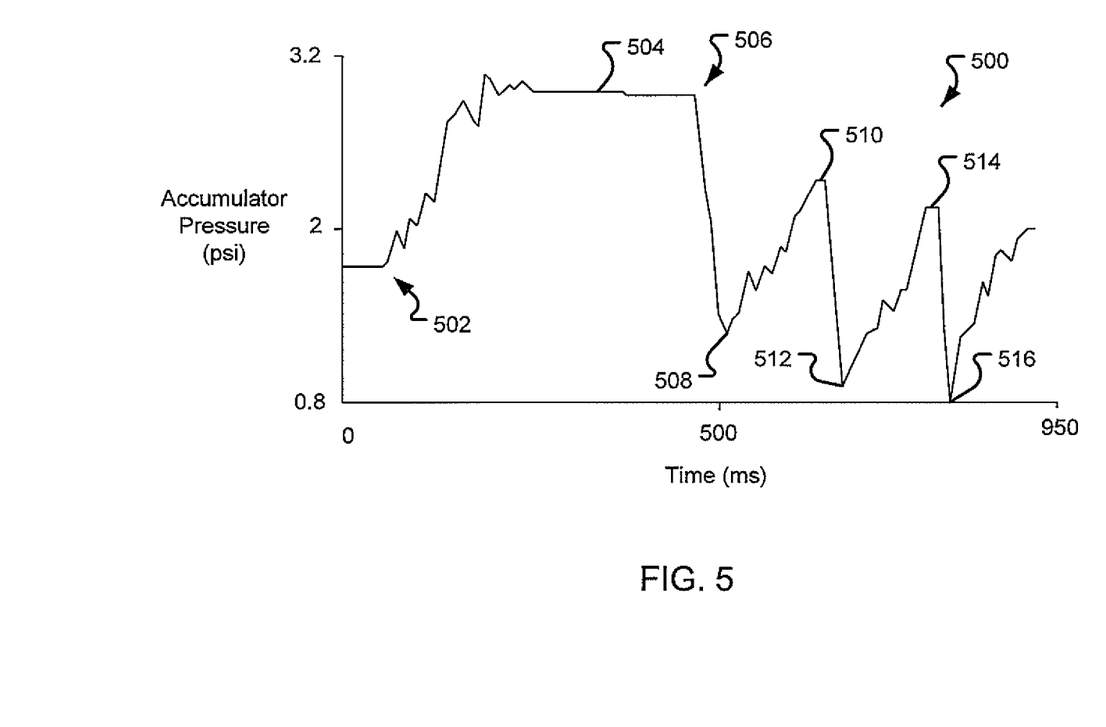
FIG. 5 illustrates an embodiment of an inverse sawtooth pressure wave train as may be generated by the purge system of FIG. 2 using the method of FIG. 4 to purge a single sensor tube.

This results in the generation of a pressure wave train in the shape of an inverse sawtooth as shown in FIG. 5 discussed below. The inverse sawtooth pressure wave train (descending ramp) generated through the tube advances the bolus away from the accumulator. The wave train is referred to as descending ramp or inverse sawtooth as, in an embodiment, the pressure of each successive discharge is slightly less as the delay period between individual purges may not be sufficient to fully recharge the accumulator to the previous pressure level.

Figure 1:
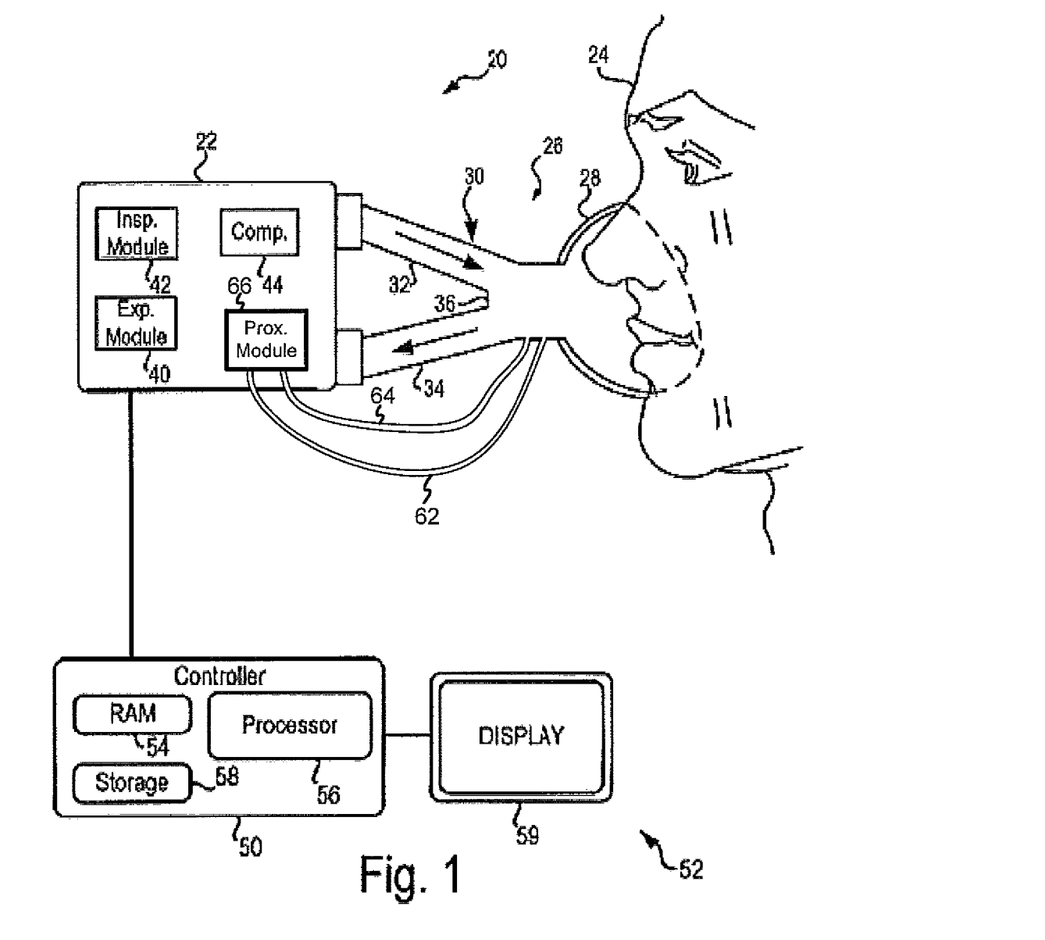
FIG. 1 illustrates an embodiment of a ventilator connected to a human patient.

FIG. 1 illustrates an embodiment of a ventilator 20 connected to a human patient 24. Ventilator 20 includes a pneumatic system 22 (also referred to as a pressure generating system 22) for circulating breathing gases to and from patient 24 via the ventilation tubing system 26, which couples the patient to the pneumatic system via physical patient interface 28 and ventilator circuit 30. Ventilator circuit 30 could be a two-limb or one-limb circuit for carrying gas to and from the patient. In a two-limb embodiment as shown, a wye fitting 36 may be provided as shown to couple the patient interface 28 to the inspiratory limb 32 and the expiratory limb 34 of the circuit 30.

The present systems and methods have proved particularly advantageous in invasive settings, such as with endotracheal tubes. However, condensation and mucus buildup do occur in a variety of settings, and the present description contemplates that the patient interface may be invasive or non-invasive, and of any configuration suitable for communicating a flow of breathing gas from the patient circuit to an airway of the patient. Examples of suitable patient interface devices include a nasal mask, nasal/oral mask (which is shown in FIG. 1), nasal prong, full-face mask, tracheal tube, endotracheal tube, nasal pillow, etc.

Pneumatic system 22 may be configured in a variety of ways. In the present example, system 22 includes an expiratory module 40 coupled with an expiratory limb 34 and an inspiratory module 42 coupled with an inspiratory limb 32. Compressor 44 or another source or sources of pressurized gas (e.g., pressured air and/or oxygen controlled through the use of one or more gas regulators) is coupled with inspiratory module 42 to provide a source of pressurized breathing gas for ventilatory support via inspiratory limb 32.

The pneumatic system may include a variety of other components, including sources for pressurized air and/or oxygen, mixing modules, valves, sensors, tubing, accumulators, filters, etc. Controller 50 is operatively coupled with pneumatic system 22, signal measurement and acquisition systems, and an operator interface 52 may be provided to enable an operator to interact with the ventilator (e.g., change ventilator settings, select operational modes, view monitored parameters, etc.). Controller 50 may include memory 54, one or more processors 56, storage 58, and/or other components of the type commonly found in command and control computing devices.

The memory 54 is computer-readable storage media that stores software that is executed by the processor 56 and which controls the operation of the ventilator 20. In an embodiment, the memory 54 comprises one or more solid-state storage devices such as flash memory chips. In an alternative embodiment, the memory 54 may be mass storage connected to the processor 56 through a mass storage controller (not shown) and a communications bus (not shown). Although the description of computer-readable media contained herein refers to a solid-state storage, it should be appreciated by those skilled in the art that computer-readable storage media can be any available media that can be accessed by the processor 56. Computer-readable storage media includes volatile and non-volatile, removable and non-removable media implemented in any method or technology for storage of information such as computer-readable instructions, data structures, program modules or other data. Computer-readable storage media includes, but is not limited to, RAM, ROM, EPROM, EEPROM, flash memory or other solid state memory technology, CD-ROM, DVD, or other optical storage, magnetic cassettes, magnetic tape, magnetic disk storage or other magnetic storage devices, or any other medium which can be used to store the desired information and which can be accessed by the processor 56.

As described in more detail below, controller 50 issues commands to pneumatic system 22 in order to control the breathing assistance provided to the patient by the ventilator. The specific commands may be based on inputs received from patient 24, pneumatic system 22 and sensors, operator interface 52 and/or other components of the ventilator. In the depicted example, operator interface includes a display 59 that is touch-sensitive, enabling the display to serve both as an input user interface and an output device.

The ventilator 20 is also illustrated as having a proximal sensor module (the "Prox. Module" in FIG. 1) 66. The proximal sensor module 66 includes at least one sensor, such as a pressure sensor, that is connected to some location in the patient circuit 30 or patient interface 28 by one or more sensor tubes 62, 64. In the embodiment shown, two sensor tubes 62, 64 connect the proximal sensor module 66 to a location in the wye fitting 36. As is known in the art, for the differential pressure measurement system to operate, a resistance to flow is placed between the flow outlets of the two sensor tubes 62, 64. In alternative embodiments, sensor tubes may connect to the ventilator tubing system 26 at any location including any limb of the circuit 30 and the patient interface 28. It should be noted that regardless of where the sensor tubes connect to the tubing system 26, because it is assumed that there is very little or no leakage from the tubing system 26 all gas discharged through the sensor tubes into the ventilator tubing system 26 will ultimately be discharged from the ventilator through the patient circuit 30 and expiratory module 40. The use of sensor tubes as part of various different measurement systems is known in the art.

In the embodiment shown, the proximal sensor module 66 includes a sensor tube purging system that purges the sensor tubes by repeatedly discharging gas through the sensor tubes into the ventilator circuit 30. The sensor tube purging system and functions are discussed in greater detail with reference to FIG. 2.

Although FIG. 1 illustrates an embodiment have two sensor tubes 62, 64 and one proximal sensor module 66, any number of sensor tubes may be used depending on the number and types of proximal sensors. For example, in some embodiments module 66 couples to three (3) tubes, with two (2) tubes used for a differential pressure sensor function and the third tube used for an alternative function such as gas composition analysis, orientation or other alternative sensors, or the like. All of the sensors may be housed in a single proximal sensor module 66 or they may be separated into different modules 66.

Furthermore, a proximal sensor module 66 may be integrated into the ventilator 20 as shown, or may be a completely independent module. If independent, the proximal flow module 66 may be adapted to detect the current phase of a patient's breathing cycle in order to synchronize the purging of the sensor tubes with specific breathing phases, such as the inspiratory phase or the exhalation phase or other conditions such as respiratory maneuvers or user-initiated purging.

Each proximal sensor module 66 may provide its own purging or a single sensor tube purge system may be provided, which may be a module incorporated into a proximal sensor module 66 or may be an independent purge module (e.g., a user-generated "purge now" command).

Figure 2:
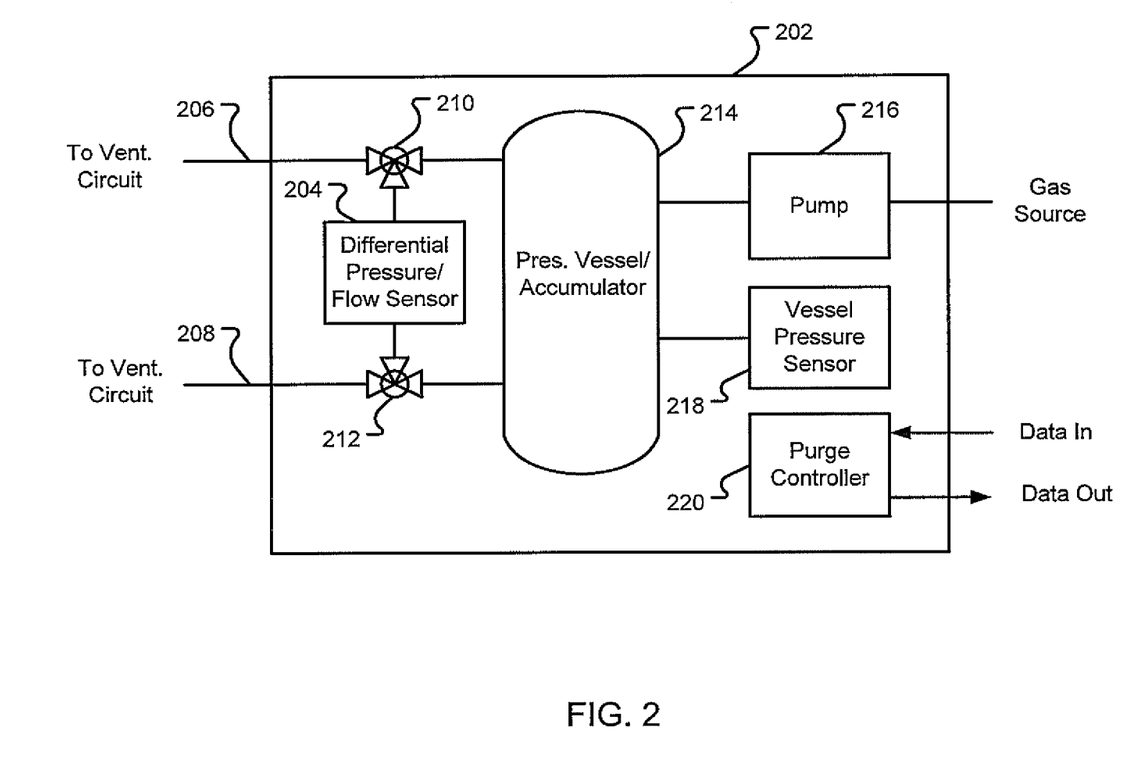
FIG. 2 illustrates an embodiment of a proximal sensor module that includes a sensor tube purging system.

FIG. 2 illustrates an embodiment of a proximal sensor module that includes a sensor tube purging system. The proximal sensor module 202 may be implemented as an independent, stand-alone module, e.g., as a separate card either inside the ventilator or within a separate housing associated with the proximal flow sensor. Alternatively, the proximal sensor module 202 may be integrated with components of the ventilator or another device, e.g., built into a ventilator control board. In yet another embodiment, the sensor tube purge system may be implemented independently from the proximal sensor 204, for example as an in-line module between the sensor and the patient circuit, in which case the module of FIG. 2 would not include the proximal sensor 204.

In the embodiment shown, a proximal sensor module 202 is illustrated having a differential pressure/flow sensor 204 connected to two sensor tubes 206, 208 that are subsequently attached to the ventilator tubing system (not shown). Sensor tubes used in conjunction with proximal sensors may have relatively small internal diameters. For example, tube diameters may be less than about 10 millimeters (mm), less than about 1 mm, or even smaller. Such sensor tubes are prone to blockage and, also because of their small diameters, are relatively more detrimentally affected by inner surface contamination even when not completely occluded.

In the embodiment shown, the differential pressure sensor 204 is connected to each sensor tube 206, 208 by a corresponding valve 210, 212. The valves 210, 212 are also connected to a pressurized vessel 214, sometimes also referred to as an accumulator 214, and operate such that when a sensor tube 206, 208 is connected to the vessel 214 (thus allowing pressurized gas from the vessel to be discharged through the sensor tube to the ventilator circuit) the associated sensor tube is not connected to the pressure sensor 204. This protects the sensor 204 from damage due to the abrupt change in pressure caused when the sensor tube is purged. In another embodiment, when performing an individual purge of either sensor tube of a differential pressure sensor, the sensor may also be disconnected from the both sensor tubes. In yet another embodiment, the differential pressure sensor may always be connected to the sensor tubing regardless of whether the tubes are being purged or not. In this embodiment, the sensor 204 may or may not be disabled (turned off) to prevent damage or the recording of spurious pressure measurements.

In the embodiment shown, the purge module in the proximal sensor module 202 includes the accumulator 214, a pump 216 (or alternatively a source of pressurized gas and a regulator) for charging the accumulator 214 with gas obtained from an external source (e.g., ambient), a pressure sensor 218 for monitoring the pressure in the accumulator 214, the aforementioned valves 210, 212 and a purge controller 220 that controls the functions of the purge module. The accumulator 214 may be any appropriate size and rated to any appropriate pressure. In an embodiment because the volumes and pressures necessary to purge the typically small-diameter sensor tubes are relatively small and cost and size are always important design factors, the accumulator 214 may have a volume between about five (5) milliliters (ml) to about 20 milliliters. In a specific embodiment, the accumulator 214 volume is between about 10 ml and about 12 ml. In some embodiments, accumulator 214 is rated to hold and/or maintain pressures between about two (2) pounds per square inch (PSI) and about thirty (30) pounds per square inch, with ratings of up to about 3 psi, up to about 6 psi and up to about 8 psi used in various embodiments depending on pump size. The pump 216 may be of any type and may receive filtered air or any other gas, including respiratory gas obtained directly from the ventilator.

For example, in an embodiment, when power is applied to the pump 216, gas from the gas source is pumped under pressure into the accumulator 214. When power is removed from the pump 216, the pump contains a suitable structure such that the pressure built up in the accumulator 214 does not discharge back through the pump. Such structure provides the function of a check valve without requiring an extra component.

In the embodiment shown, the accumulator pressure sensor 218 is provided to obtain information concerning the pressure within the vessel 214. From this information, the amount of gas used during purging can be determined. Depending on the embodiment the raw pressure data may be provided to the ventilator for use in calculating the gas flow through the patient circuit or may be provided to the purge controller 220, which calculates the purge volume and provides that data to the ventilator. Such a calculation would be performed based on the pressure changes observed during the purge cycle and previously determined data characterizing the volume, compliance and other parameters of the purge module as is known in the art.

In the embodiment shown, the purge controller 220 controls the purging of the sensor tubes 206, 208 by controlling the opening and closing of the valves 210, 212 and the pressurizing of the accumulator 214 by the pump 216. In an embodiment, the purge controller 220 includes a microprocessor executing software stored either on memory within the processor or in a separate memory cache. The purge controller 220 may or may not be involved in the transmission of sensor data from the differential pressure/flow sensor 204 to other devices or components such as the ventilator (e.g., the sensor 204 may directly output its data signal to the ventilator).

As discussed above, the controller 220 may also interface between the ventilator and the purge system to provide information such as the status of the purge system (e.g., currently discharging, time since last discharge, currently in a purge cycle, time since last purge cycle, purge failure error due to possible occlusion of a sensor tube, time/duration of last discharge, time until next discharge, current interval setting, component failure, etc.) and the amount of purge gas delivered into the patient circuit. The controller 220 may also receive information from external sources such as modules of the ventilator, in particular information concerning the current breathing phase of the patient so that the purge system can synchronize its operations with the delivery of gas to the patient, and user interfaces. The information received may include user-selected or predetermined values for various parameters such as the purge cycle interval (e.g., perform a purge cycle every 10 minutes), accumulator pressure, between-discharges delay period, individual purge/discharge interval, etc. The information received may further include directions such as a ventilator-generated purge command or an operator command to perform a purge cycle at the next opportunity (e.g., an automatic or a manual purge command). The controller 220 may also include an internal timer so that individual purges and purge cycles can be performed at a user or manufacturer specified interval.

Depending on the embodiment, the controller 220 may also monitor the pressure in the accumulator 214 (via the vessel pressure sensor 218) when controlling the pump 216 so that specified pressures are obtained at different points in the purge cycle. In an alternative embodiment, the controller 220 may rely on timing alone to control the operation of the purge system, for example such as when there is no sensor 218 provided, by opening and closing valves and operating the pump for specified lengths of time.

In an embodiment, the proximal sensor module 202 may be independent of the ventilator in that it determines based on its own internal logic (which may take into account data from the ventilator, directly from the sensor 204, the accumulator sensor 218 or other sources) when to perform purges of the sensor tubes. In an alternative embodiment, the proximal sensor module 202 may be less than independent of the ventilator or, even, purely a slave to the commands provided by the ventilator and containing little or no internal decision making or processing capabilities, in which case the logic and methods described herein may be performed by the ventilator's processors.

In an alternative embodiment (not shown), alternative systems for providing pressured gas for purging may be used. For example, in an embodiment the pump 216 and accumulator 214 may be replaced with a regulator (not shown) and a valve that regulates pressure from an external pressurized gas source. Many other systems for providing pressurized gas are known in the art. Although the systems described herein are expedient given the current design constraints encountered by the inventors, any suitable pressurized gas system may be used and are considered within the scope of this disclosure.

In an alternative embodiment, the module 202 does not include a vessel pressure sensor 218 and does not have the ability to measure the pressure in the accumulator 214. In this case, control of the pump 216 and knowledge of the pump's specifications and the accumulator size may be used to determine the amount of gas injected during an individual purge event or the fills purge cycle into the patient circuit.

FIG. 2 illustrates a simple embodiment having two sensor tubes. In different embodiments, more or fewer sensor tubes may be used by the proximal sensor module, each of which is adapted to be purged by the purging system.

Figure 3:
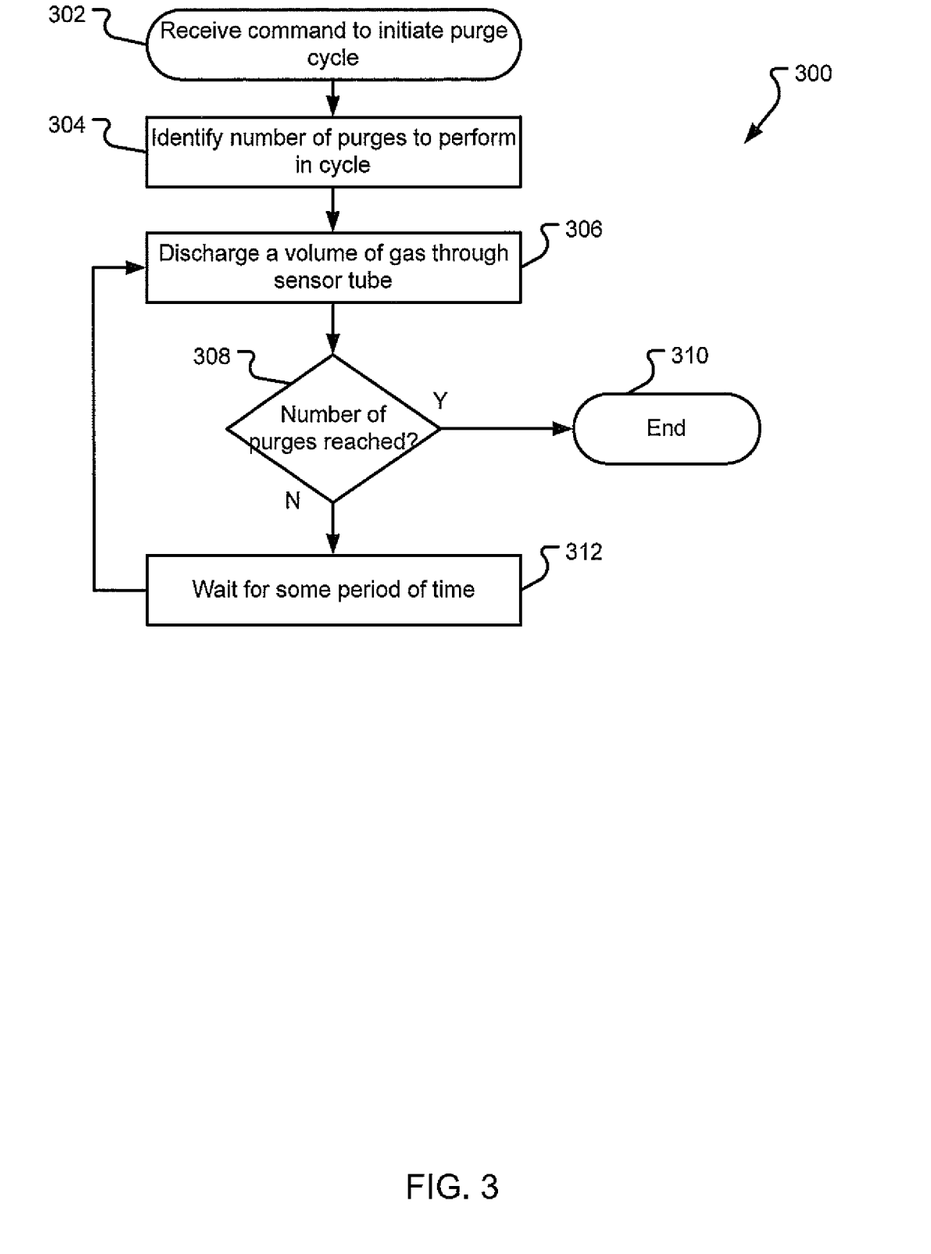
FIG. 3 illustrates an embodiment of a method of purging a sensor tube connecting a patient circuit of a medical ventilator to a sensor.

FIG. 3 illustrates an embodiment of a method of purging a sensor tube connecting a patient circuit of a medical ventilator to a sensor. The embodiment illustrated in method 300 in simple terms can be described as intermittently and/or repeatedly discharging gas through a sensor tube into the patient circuit. Each discharge is followed by some period in which there is no discharge. This results in the creation of a "pressure wave train" being created in the sensor tube over time during the purge cycle. Because of the fluid dynamics of the transport process in the tubes, it is believed that this pressure wave train is more effective than a single discharge having the same duration as the purge cycle. Although any duration may be used for a gas discharge, in some embodiments, gas discharges having a fixed duration of less than 100 milliseconds (ms) have been contemplated. Specifically, embodiments having a purge duration of equal to or less than about 100 ms, about 50 ms, about 25 ms and about 10 ms per discharge have been identified.

Returning to FIG. 3, the general method 300 shown starts with a command to initiate a purge cycle to purge the sensor tube or tubes in a command receipt operation 302. This may include receipt of an actual direction from a user interface, from a module of the ventilator system or from the purge module itself, such as in response to an internal timing indicating the expiration of a purge interval.

The method 300 further identifies the number of individual purges, also referred to herein as "discharges", to be performed in the purge cycle in a discharge number identification operation 304. Depending on the embodiment, this may include accessing a predetermined number stored in memory. The number itself may be provided by the manufacturer or may have been selected by the operator. In another embodiment, the number of discharges to be performed may be calculated based on information such as the time since the last purge cycle, ventilator conditions such as operating pressure, temperature or humidity, the patient size or patient condition, the anticipated amount of time in the breathing phase during which the purge cycle is to be performed, or the number of discharges remaining in an interrupted purge cycle.

The method 300 performs at least one discharge through a selected sensor tube, illustrated by the purge operation 306. This involves discharging gas through the sensor tube into the patient circuit. The discharge may be of a fixed duration, of a fixed pressure drop or of some combination of time and pressure factors such as discharge for a fixed period of time or until a minimum pressure drop is reached. As discussed elsewhere, this operation 306 may not be performed unless a determination that the appropriate breathing phase is occurring.

This purge operation 306 is then repeated, after a suitable delay, until the cycle is completed by performing the identified number of discharges through the sensor tube. This is illustrated in the flow diagram of FIG. 3 by the determination operation 308 that checks to see if the number of individual purges/discharges to be performed in the purge cycle have been completed. If the number has been completed, then the method ends in a termination operation 310 which includes any necessary shutdown procedures.

If the number has not been completed, there is a delay operation 312, after which another purge operation 306 is performed. The delay operation 312 may be for a fixed period or a variable period (such as the time necessary to recharge an accumulator to a specified pressure). In an embodiment, the delay is a fixed period selected to allow an accumulator to recharge based on the anticipated pump performance. In another embodiment, the delay is a determined period of time selected to allow another purge operation 306 to occur during a subsequent desired breath phase cycle (e.g., during another patient exhalation phase).

Figure 4:
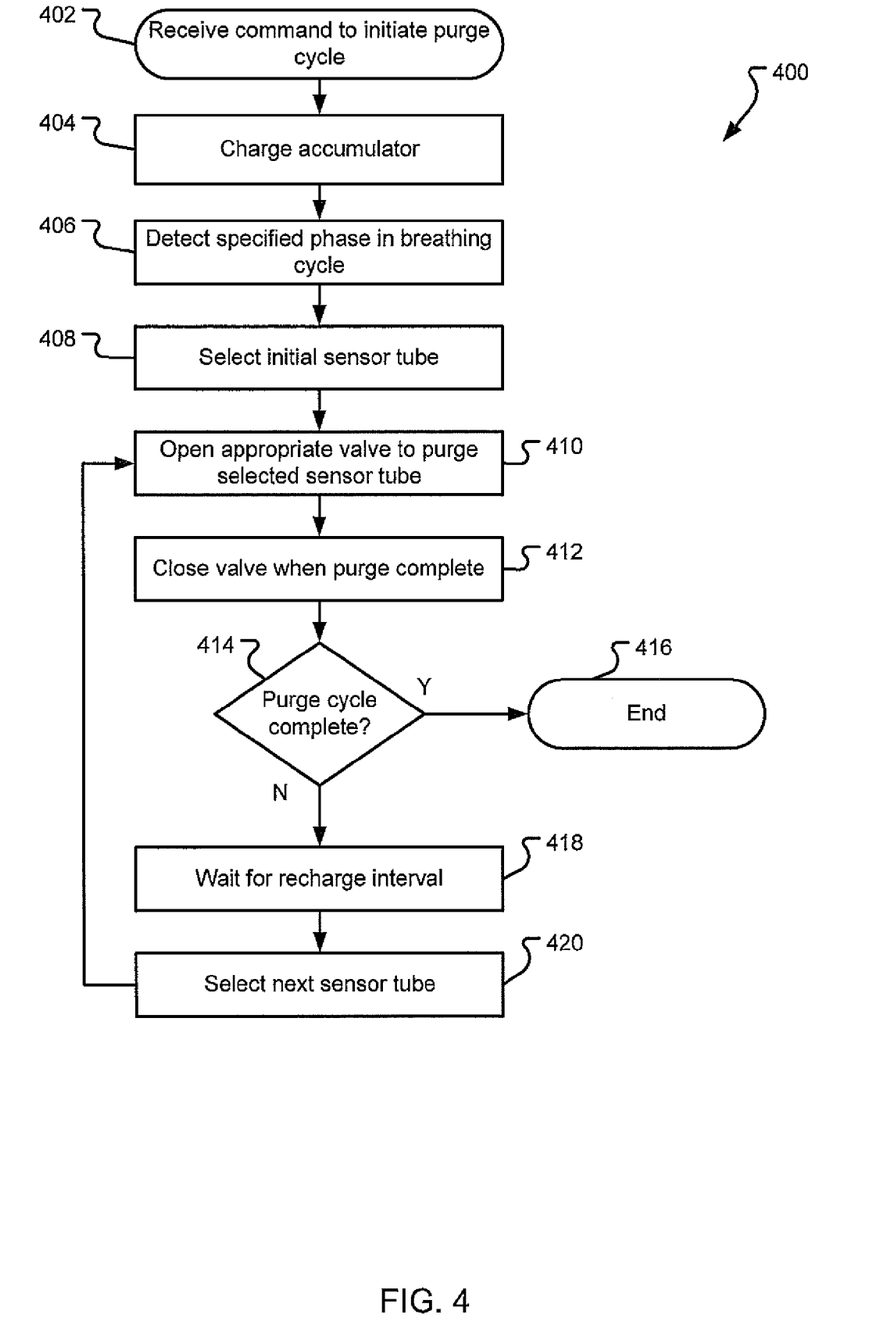
FIG. 4 illustrates an embodiment of a method of purging a sensor tube connecting a patient circuit of a medical ventilator to a sensor using a purge system similar to that shown in FIG. 2.

FIG. 4 illustrates an embodiment of a method of purging a sensor tube connecting a patient circuit of a medical ventilator to a sensor using a purge system similar to that shown in FIG. 2. The method 400 represents an embodiment of the general method 300 but provides additional details specific to an accumulator and pump embodiment as shown in FIG. 2.

As illustrated, the method 400 starts with a command to perform purge cycle to purge the sensor tube or tubes in a command receipt operation 402. This may include receipt of an actual direction from a user interface or another module of the ventilator system or may be the result of a timer expiring.

The method 400 also includes an accumulator charge operation 404. This operation 404 charges the accumulator to some initial pressure prior to the first purge being performed. This may include monitoring the accumulator pressure so that a specified pressure is obtained or charging the accumulator for some fixed period of time using a known charging method or equipment. Although illustrated as the second operation in the embodiment shown in FIG. 4, this operation 404 may be performed at any time after the last purge cycle and prior to the first purging operation of the cycle initiated by the command receipt operation 402.

The method 400 also illustrates a detection operation 406 that determines, based on the current phase in the breathing cycle (e.g., inspiratory phase, expiratory phase, pause maneuver, or specified locations within a particular phase such as inspiratory hold or after a delay period from onset exhalation), if a purge can be performed.

This operation 406 is provided to illustrate that the performance of purges may be very specifically synchronized with the cyclic delivery of therapeutic gas to the patient and the operation of the ventilator. Although not illustrated, in an alternative embodiment the detection operation 406 is an ongoing operation throughout the purge cycle that prevents any purge (i.e., open and close valve operations 410, 412) from occurring when a purge is inappropriate or undesirable. In an embodiment, this may be effected through the use of a "purge enable" signal provided from a ventilator module to the purge system in which the detection operation 406 simply involves monitoring of the purge enable signal. The purge enable signal is generated by the ventilator based on its monitoring of the breathing cycle and its monitoring of any manual intervention via the user interface which may preclude the occurrence of purging (such as an Inspiratory hold maneuver). Thus, if purges should only be performed during exhalation, for example, the purge enable signal would indicate that a purge is allowed when the ventilator is in the exhalation phase of the breathing cycle. In an alternative embodiment, different information may be provided to or obtained by the purge system (such as pressure and flow data or a data signal indicative of the current phase of the breathing cycle) from which the purge controller can make it own determination that a purge can be performed.

In some embodiments, purge initiation occurs during a patient exhalation only. The purge system controller may receive an exhalation signal from a ventilator controller, after the ventilator controller has determined the beginning of patient exhalation. In this manner, the purge operation is keyed to the ventilator-determined patient breath phase.

It should also be noted that in an embodiment (not shown), the detection operation 406 may also interrupt an ongoing purge cycle in the event that it detects that conditions have changed (e.g., detection that the ventilator has triggered from exhalation phase to inhalation phase, the "purge enable" signal changes, etc.) and that discharging gas through a sensor tube is no longer appropriate. In this embodiment, as part of interrupting the purge cycle, the necessary operations may be performed so that the purge system picks up where it left off upon the next detection of conditions that allow for purging. In this way, for example, the purge cycle may be performed over a set of consecutive breaths with one or more discharges performed during the appropriate phase in each of a group of breaths until the purge cycle is complete.

As part of initiating a purge cycle, the method 400 further includes selecting an initial sensor tube to be the first tube purged. This is illustrated by the select initial tube operation 408 and is provided in order to show that, in embodiments in which there are two or more tubes to be purged, different tubes may be purged first during different purge cycles, thus allowing the system to alternate which tube is purged first.

In an open valve operation 410, the selected tube is then purged by opening its associated valve that connects it to the accumulator. As discussed above, this operation 410 may also include disabling or disconnecting the sensor associated with the selected tube or from all tubes. By opening the valve, gas in the accumulator which has been deliberately raised to a higher pressure than gas in the patient circuit is allowed to discharge through the selected sensor tube. In some embodiments, pump 216 continues to pump gas into the accumulator when the accumulator valve to the selected tube is open. In this manner, some gas may pass through accumulator and continue down the selected tube before the valve is closed.

After some period of time, the valve is then closed in a close valve operation 412. Once the valve is closed, continued pump action operates to raise gas pressure within accumulator to a desired pressure, or for a desired period of time. The time between opening the valve and closing it may be a predetermined fixed time such as about 200, 150, 100, 50, 25, or 10 ms. Alternatively, the time may be variable based on some other parameter or condition, such as the time necessary to observe some predefined pressure rise in the accumulator or some other effect related to the purge. The time may be the same every time a valve is closed to charge the accumulator or may be varied.

After the close valve operation 412, a determination operation 414 checks to see if the purge cycle is complete. In an embodiment, this may involve determining how many discharges should be performed through each sensor tube and comparing this number to a counter maintained of the number of times valves have been opened in the current cycle. Other methods are also possible.

If the purge cycle is complete (e.g., each sensor tube has been purged the appropriate number of times), then the purge method may end in a termination operation 416. The termination operation 416 may include performing various housekeeping functions such as emptying the accumulator, recharging the accumulator, resetting the proximal sensor, generating and/or transmitting data related to the purge cycle such as the amount of gas discharged into the patient circuit and updating timers and counters.

If the purge cycle is not complete (e.g., one or more sensor tubes have not been purged the appropriate number of times), then a waiting operation 418 may be performed. In a single sensor tube embodiment, the waiting operation 418 allows the purging flow through the sensor tube to stop and the pressure in the tube to equilibrate to the patient circuit pressure. This operation 418 is optional in multi-tube systems as the same function may be achieved by simply purging another tube without delay between the closing of the valve of the first tube and opening the valve of the next tube. However, even in a multi-tube embodiment, if the accumulator is relatively small, a waiting operation 418 may be used to allow sufficient time for the pump to recharge the accumulator.

The duration of the waiting period 418 may be predetermined by the operator or manufacturer and may be same every time it is performed. Alternatively, the waiting period may be of a variable duration based on some other factor, such as the duration necessary to allow the accumulator to return to a target threshold. Although any duration may be used for the waiting operation 418, in embodiments, delay between successive valve openings having a fixed duration of less than 300 ms have been contemplated to allow the accumulator to be recharged to at least some extent before the next purge cycle. Specifically, embodiments having a delay duration of equal to or less than about 200 ms, 175 ms, 150 ms and 100 ms between purges have been identified.

After the waiting operation 418, the next tube to be purged is purged. This is illustrated by the select next tube operation 420 and then the flow returning to the open selected valve operation 410. In an embodiment, tubes may be purged in a fixed order so that after the initial tube has been selected the purge cycle proceeds to purge each tube in the order until the all tubes have been purged once and then repeats the process until all tubes have be purged the appropriate number of times. In this embodiment, the select next tube operation 420 consists essentially of selecting the next tube in the purge order. Other methods of cycling through multiple tubes are possible and any suitable method may be used herein.

Regarding operation of the pump, although not explicitly illustrated in FIG. 4, in an embodiment the pump may be operated continuously throughout the purging of the sensor tubes, that is the pump operates continuously from the first instance of a valve being opened in an open valve operation 410 until the determination operation 414 determines that the cycle is complete. In this embodiment, the pump is operating during periods where a valve is open and there is flow through a sensor tube and during the waiting operation 418 during which the accumulator is being recharged prior to the next purge. Thus, in this embodiment the waiting operation 418 could also be characterized as a recharging operation during which the vessel is recharged with gas. In alternative embodiments, the pump may be operated only during specified operations, such as only during the waiting operation 418 and/or only when certain conditions occur, such as the pressure in the accumulator falls below some threshold amount.

FIG. 5 illustrates an embodiment of an inverse sawtooth pressure wave train as may be generated by the purge system of FIG. 2 using the method of FIG. 4. In the embodiment shown, the trace 500 of the accumulator pressure against time is illustrated through a purge cycle having three discharges. At some time 502 (approximately at 50 ms) the purge system receives a command to perform a purge cycle. The accumulator is then pressurized by the pump for either a fixed period of time or until a specified pressure is reached, which raises the pressure up to the initial pressure level 504.

The system then waits until it detects 506 that it is time to perform the purge (approximately at 475 ms), e.g., the system detects the breath phase cycling to exhalation or receives a purge enable signal. The first selected sensor tube is then purged via the opening of the appropriate valve which allows the pressure to be released through the sensor tube into the patient interface. This results in a rapid drop in the pressure within the accumulator.

After purging, the valve is then closed after purging the sensor tube. In the embodiment illustrated, the purge period is fixed at 25 ms at which point the pressure has reached some lower value 508 (approximately 1.3 psi) This completes one purge of the first sensor tube.

In the embodiment illustrated, the pump then recharges the accumulator for 125 ms resulting in the pressure increasing to some second pressure 510 (approximately 2.3 psi) and the next purge is then performed. After 25 ms of purging, the pressure in the accumulator has then dropped to some third level 512 (approximately 0.8 psi) and the valve is again closed and the pressure is allowed to recharge for another 125 ms bringing the accumulator up to some pressure level 514. One last purge is then performed in which the pressure in the accumulator falls to an even lower level 516. In the embodiment shown, the pump remains in operation for some period of time which raises pressure in the accumulator to some level after the purging cycle has been completed.

In some embodiments, a purge operation will require more than one breath phase to be completed. For example, neonate patients typically have very short breath cycles. For purge operations that only should occur during patient exhalation, a single exhalation phase of a neonate patient may be of insufficient duration to allow a complete purge operation. In this embodiment, the purge operation may be started during a first exhalation, stopped when the first exhalation ends, and resumed during a second exhalation. In some embodiments, the beginning and end of the exhalation phase of each patient's breath is determined by the ventilator controller, and the inspiration and/or expiration signals are sent from the ventilator controller to the purge system controller.

In some embodiments, purge system controller controls the order of the sensor tubes to be purged. For example in a system with two sensor tubes (e.g., tubes A and B) to be purged, the purge system controller may start a purge operation with the tube A, and then alternate purging tubes A and B until the purge cycle is completed. If the sensor tubes are to be purged a like number of times for each purge cycle, then the purge cycle would end with a purge of tube B. For the subsequent purge operation of the same system, the purge system controller may start the purge operation with tube B.

In other embodiments, purge system controller operates to purge two or more sensor tubes simultaneously. This may occur, for example, with purge systems having sufficiently high pressure, sufficiently large accumulators, or some combination of these factors or additional factors.

It will be clear that the systems and methods described herein are well adapted to attain the ends and advantages mentioned as well as those inherent therein. Those skilled in the art will recognize that the methods and systems within this specification may be implemented in many manners and as such are not to be limited by the foregoing exemplified embodiments and examples. For example, the operations and steps of the embodiments of methods described herein may be combined or the sequence of the operations may be changed while still achieving the goals of the technology. In addition, specific functions and/or actions may also be allocated in such as a way as to be performed by a different module or method step without deviating from the overall disclosure. In other words, functional elements being performed by a single or multiple components, in various combinations of hardware and software, and individual functions can be distributed among software applications. In this regard, any number of the features of the different embodiments described herein may be combined into one single embodiment and alternate embodiments having fewer than or more than all of the features herein described are possible.

While various embodiments have been described for purposes of this disclosure, various changes and modifications may be made which are well within the scope of the present invention. For example, if the capabilities of the system allow all sensor tubes could be purged simultaneously, thus reducing the overall time necessary to complete the purge cycle at the expense of purge system cost. Numerous other changes may be made which will readily suggest themselves to those skilled in the art and which are encompassed in the spirit of the disclosure and as defined in the appended claims.

Unless otherwise indicated, all numbers expressing quantities, properties, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention.

As used herein, "about" refers to a degree of deviation based on experimental error typical for the particular property identified. The latitude provided the term "about" will depend on the specific context and particular property and can be readily discerned by those skilled in the art. The term "about" is not intended to either expand or limit the degree of equivalents which may otherwise be afforded a particular value. Further, unless otherwise stated, the term "about" shall expressly include "exactly," consistent with the discussions regarding ranges and numerical data. Concentrations, amounts, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 4 percent to about 7 percent" should be interpreted to include not only the explicitly recited values of about 4 percent to about 7 percent, but also include individual values and sub-ranges within the indicated range. Thus, included in this numerical range are individual values such as 4.5, 5.25 and 6 and sub-ranges such as from 4-5, from 5-7, and from 5.5-6.5, etc. This same principle applies to ranges reciting only one numerical value. Furthermore, such an interpretation should apply regardless of the breadth of the range or the characteristics being described.

What is claimed is:

1. A method of purging two or more sensor tubes in a medical ventilator providing ventilation to a patient, the method comprising:
   a) charging a vessel with gas to a first predetermined pressure;
   b) detecting initiation of a first exhalation phase in a breathing cycle of the patient;
   c) after step b), releasing gas from the vessel through a first one of the sensor tubes into a patient circuit of the ventilator for a first predetermined period of time;

d) after step c), recharging the vessel with gas to a second predetermined pressure different from the first predetermined pressure; and e) after step d), releasing gas from the vessel through a second one of the sensor tubes into the patient circuit of the ventilator for a second predetermined period of time.

2. The method of claim 1 further comprising:
f) after step e), repeating step d);
g) after step f), repeating steps c), d) and e).

3. The method of claim 2 further comprising:
h) after step g), repeating steps f) and g) at least once.

4. The method of claim 3 further comprising:
continuously operating a pump to pump gas into the vessel during steps c), d), e), f), g) and h).

5. The method of claim 3 further comprising:
performing steps f) and g) during a subsequent exhalation phase after the first exhalation phase in the breathing cycle of the patient.

6. The method of claim 2 further comprising:
performing step e) during a subsequent exhalation phase after the first exhalation phase in the breathing cycle of the patient.

7. The method of claim 2 further comprising:
performing steps f) and g) during a subsequent exhalation phase after the first exhalation phase in the breathing cycle of the patient.

8. The method of claim 1 wherein charging the vessel further comprises:
engaging a pump to pump the gas into the vessel until the first predetermined pressure is obtained.

9. The method of claim 1 further comprising:
continuously operating a pump to pump gas into the vessel during steps c), d) and e).

10. The method of claim 9 wherein step d), recharging the vessel, further comprises:
waiting for a third predetermined period of time between an end of step c), releasing the gas through the first one of the sensor tubes, and an initiation of step e), thereby allowing the pump to recharge the vessel with gas during the third predetermined period of time.

11. The method of claim 1 wherein the first predetermined period of time and the second predetermined period of time are equal.

12. The method of claim 1 wherein step a) is performed prior to step b).

13. The method of claim 1 wherein each of the first predetermined period of time and the second predetermined period of time are less than about 100 milliseconds.

14. The method of claim 1 wherein each of the first predetermined period of time and the second predetermined period of time are less than about 50 milliseconds.

15. The method of claim 1 wherein each of the first predetermined period of time and the second predetermined period of time are less than about 25 milliseconds.

16. The method of claim 1 wherein each of the first predetermined period of time and the second predetermined period of time are less than about 10 milliseconds.

17. The method of claim 1, further comprising:
detecting an end of the first exhalation phase in the breathing cycle of the patient prior to the performance of step e);
performing step e) during a subsequent exhalation phase after the first exhalation phase in the breathing cycle of the patient.

18. A method of purging a sensor tube connecting a patient circuit of a medical ventilator to a sensor, the method comprising:
repeatedly discharging gas through a first sensor tube into the patient circuit, wherein each gas discharge has a fixed duration of less than 100 milliseconds and each gas discharge is separated from a prior gas discharge by about 200 milliseconds.

19. The method of claim 18 further comprising:
pneumatically disconnecting a sensor associated with the first sensor tube during each gas discharge.

20. The method of claim 18 further comprising:
disabling the sensor associated with the first sensor tube during each gas discharge.

21. The method of claim 18 further comprising:
repeatedly and alternately discharging gas into the patient circuit through the first sensor tube and a second sensor tube.

22. The method of claim 18 wherein each discharging operation further comprises:
opening a valve connecting the first sensor tube to a pressurized vessel for the fixed duration of time.

23. The method of claim 22 further comprising:
repeatedly discharging gas at a decreasing pressure.

24. The method of claim 22 further comprising:
monitoring pressure in the pressurized vessel during the discharging operation.

25. The method of claim 18 further comprising:
monitoring a breathing cycle of a patient connected to the medical ventilator; and
discharging gas only during a specified phase of the breathing cycle.

26. The method of claim 25 further comprising:
discharging gas only during an exhalation phase of the breathing cycle.

27. The method of claim 25 further comprising:
discharging gas during multiple consecutive specified phases of the breathing cycle.

28. The method of claim 18 further comprising:
receiving a user input selecting the fixed duration of each gas discharge.

29. The method of claim 18 further comprising:
determining an amount of gas discharged during at least one gas discharge;
including the amount of gas discharged in a determination of gas flow in the patient circuit.

30. A pressure support system comprising:
a pressure generating system adapted to generate a flow of breathing gas;
a ventilation system including a patient circuit;
at least one circuit sensor in fluid communication with the patient circuit via one or more sensor tubes; and
a sensor tube purge module adapted to initiate a purge cycle that purges the sensor tubes, wherein each purge cycle includes repeatedly discharging gas through the sensor tubes into the patient circuit, wherein each gas discharge has a fixed duration of less than 100 milliseconds and each gas discharge is separated from a prior gas discharge by about 100 milliseconds.

31. The system of claim 30 wherein the ventilation system monitors a patient's breathing cycle and the sensor tube purge module discharges gas through a sensor tube only during a predetermined phase of the patient's breathing cycle as determined by the ventilation system.

32. The system of claim 30 wherein the sensor tube purge module further comprises: a pressure vessel from which the gas discharged through the sensor tubes is obtained.

33. The system of claim 32 wherein the sensor tube purge module further comprises: at least one valve that controls a flow of gas from the pressure vessel through one or more of the sensor tubes.

34. The system of claim 32 wherein the sensor tube purge module further comprises:
at least one vessel sensor that monitors a pressure in or a flow of gas from a pressurized vessel; and
wherein the sensor tube purge module determines a volume of gas discharged through at least one sensor tube into the patient circuit based on data obtained from the at least one vessel sensor.

35. The system of claim 32 wherein the sensor tube purge module further comprises:
a pump that delivers pressurized gas to a pressurized vessel.

36. The system of claim 30 wherein the sensor tube purge module further comprises:
at least one sensor interface valve that disconnects the at least one circuit sensor from its associated sensor tube when gas is discharged through the associated sensor tube.

37. The system of claim 30 wherein the sensor tube purge module further comprises:
at least one regulator that controls flow of gas from a pressurized gas source through the sensor tubes.

38. The system of claim 37 wherein the pressurized gas source is the pressure generating system.

39. The system of claim 30 wherein the sensor tube purge module discharges gas through only one sensor tube at a time.

40. The system of claim 30 wherein the sensor tube purge module simultaneously discharges gas through at least two sensor tubes at a time.

41. A controller for a medical ventilator comprising:
a microprocessor; and
a sensor tube purge module adapted to initiate a purge cycle that purges sensor tubes connected to sensors in the medical ventilator; wherein each purge cycle includes repeatedly discharging gas through the sensor tubes into a patient circuit, wherein each gas discharge has a fixed duration of less than 100 milliseconds and each gas discharge is separated from a prior gas discharge by about 150 milliseconds.

42. A computer-readable medium having computer-executable instructions for performing a method of purging a sensor tube connecting a patient circuit of a medical ventilator to a sensor, the method comprising:
repeatedly discharging gas through a first sensor tube into the patient circuit, wherein each gas discharge has a fixed duration of less than 100 milliseconds and each gas discharge is separated from a prior gas discharge by about 50 milliseconds.

43. The computer-readable medium of claim 42 wherein the method further comprises:
disconnecting the sensor associated with the first sensor tube during each gas discharge.

44. The computer-readable medium of claim 42 wherein the method further comprises:
repeatedly and alternately discharging gas into the patient circuit through the first sensor tube and a second sensor tube.

45. The computer-readable medium of claim 42 wherein each discharging operation further comprises:
opening a valve connecting the first sensor tube to a pressurized vessel for the fixed duration of time.

46. The computer-readable medium of claim 42 wherein each discharging operation further comprises:
monitoring a breathing cycle of a patient connected to the medical ventilator; and
discharging gas only during a specified phase of the breathing cycle.

47. The computer-readable medium of claim 42 wherein each discharging operation further comprises:
determining an amount of gas discharged during at least one gas discharge;
including the amount of gas discharged in a determination of gas flow in the patient circuit.

48. A medical ventilator system, comprising:
a processor;
a gas regulator in communication with the processor, the gas regulator adapted to regulate a flow of gas from a gas supply to a patient via a patient circuit;
a flow sensor package disposed in the patient circuit, the flow sensor package in communication with a gas accumulator; and
a pressure sensor coupled to the gas accumulator and in communication with the processor, the pressure sensor adapted to provide pressure readings in the gas accumulator to the processor,
wherein the processor is adapted to instruct the accumulator to deliver a desired amount of gas to a first line used to sense differential pressure within a flow sensor disposed in the flow sensor package when the gas accumulator reaches a first predetermined pressure based on the pressure readings provided by the pressure sensor, and
wherein after the delivery of the desired amount of gas to the first line, the processor is adapted to instruct the accumulator to deliver the desired amount of gas to a second line used to sense the differential pressure within the flow sensor disposed in the flow sensor package when the gas accumulator reaches a second predetermined pressure different from the first predetermined pressure based on the pressure readings provided by the pressure sensor.

49. The system as in claim 48, wherein the gas accumulator is adapted to hold the desired amount of gas for delivery to at least one line used to sense the differential pressure within the flow sensor package.

50. The system as in claim 49 wherein the processor is adapted to determine an initiation of a patient exhalation, and to thereafter provide a purge signal to the gas accumulator.

51. The system as in claim 48 wherein the pressure sensor is disposed remote from the flow sensor package.

* * * * *

UNITED STATES PATENT AND TRADEMARK OFFICE
CERTIFICATE OF CORRECTION

| | | |
|---|---|---|
| PATENT NO. | : 8,528,554 B2 | Page 1 of 1 |
| APPLICATION NO. | : 12/553568 | |
| DATED | : September 10, 2013 | |
| INVENTOR(S) | : Jafari | |

It is certified that error appears in the above-identified patent and that said Letters Patent is hereby corrected as shown below:

Title page, under item (75), the first inventor's name should read as follows:

Mehdi M. Jafari

Signed and Sealed this
Fourth Day of March, 2014

Michelle K. Lee
*Deputy Director of the United States Patent and Trademark Office*